United States Patent [19]
Torgerson et al.

[11] Patent Number: 5,893,883
[45] Date of Patent: Apr. 13, 1999

[54] PORTABLE STIMULATION SCREENING DEVICE FOR SCREENING THERAPEUTIC EFFECT OF ELECTRICAL STIMULATION ON A PATIENT USER DURING NORMAL ACTIVITIES OF THE PATIENT USER

[75] Inventors: Nathan A. Torgerson, White Bear Lake; Jean E. Prather, Rogers; John W. Forsberg, St. Paul; Curtis D. Kinghorn, Lino Lakes, all of Minn.

[73] Assignee: Medtronic, Inc., Minneapolis, Minn.

[21] Appl. No.: 08/847,650

[22] Filed: Apr. 30, 1997

[51] Int. Cl.$^6$ ................................................ A61N 1/36
[52] U.S. Cl. ................................................ 607/59
[58] Field of Search ................................ 607/46, 52, 59, 607/62, 63, 72

[56] References Cited

U.S. PATENT DOCUMENTS

| | | | |
|---|---|---|---|
| 4,505,275 | 3/1985 | Chen | 607/62 |
| 4,690,145 | 9/1987 | King-Smith et al. | 607/63 |
| 5,370,672 | 12/1994 | Fowler et al. | 607/58 |
| 5,653,739 | 8/1997 | Maurer et al. | 607/46 |
| 5,683,422 | 11/1997 | Rise | 607/62 |

*Primary Examiner*—William E. Kamm
*Attorney, Agent, or Firm*—Banner & Witcoff Ltd.

[57] ABSTRACT

A stimulation device for screening therapeutic effects from electrical stimulation of electrically excitable tissue. The stimulation device includes inputs such that the user can easily select the polarity, amplitude, pulse width, and pulse rate of the respective stimulation signal applied on each of the implanted electrodes. Alternatively, the stimulation device automatically sets those parameters of the stimulation signal with parameters that have historically produced high ratings of therapeutic effect. The user then enters a rating of the therapeutic effect that results from the application of those stimulation signals on the implanted electrodes. The stimulation device is designed to also include a casing such that the stimulation device is adapted to be portable. Because the stimulation device of the present invention is also inexpensive, the user can carry this device around during normal daily activities of the user during the screening process. Consequently, parameters of the stimulation device that would result in optimum therapeutic effect for normal daily activities of the user can be determined more easily and more accurately.

30 Claims, 6 Drawing Sheets

PORTABLE STIMULATION SCREENING DEVICE FOR SCREENING THERAPEUTIC EFFECT OF ELECTRICAL STIMULATION ON A PATIENT USER DURING NORMAL ACTIVITIES OF THE PATIENT USER

BACKGROUND OF THE INVENTION

1. Field of the Invention

This invention relates to a method and apparatus for screening therapeutic effects from electrical stimulation of electrically excitable tissue, and more particularly to a portable stimulation device that allows the user to configure the parameters of a respective stimulation signal applied on each of at least one implanted stimulation electrode and that stores ratings of the therapeutic effects along with the corresponding stimulation signal parameters.

2. Description of the Related Art

The use of medical devices for electrical stimulation of electrically excitable tissue is well known in the medical arts. Electrical stimulation of brain tissue has been used for tremor suppression, and electrical stimulation of peripheral nerve tissue has been used to promote blood circulation in patients having peripheral vascular disease. In addition, electrical stimulation of the brain and nerve tissue of the spinal cord has been used for pain management. Electrodes have been implanted near the spinal column of the human body to provide pain relief. The nerve tissue within the spinal column is stimulated electrically to reduce pain sensations at another part of the body.

Depending on the particularities of each different human body, the parameters of the stimulation signals applied near electrically excitable tissue are adjusted to optimize the therapeutic effect from the electrical stimulation. For example for pain management, the area of excitation within the spinal column and the intensity of excitation can be varied by corresponding adjustment of the parameters of the stimulation signals.

In order to vary the area of excitation, an array of electrodes may be implanted near the nerve tissue within the spinal column. Then, each of those electrodes can be configured to have a respective one of a positive or negative polarity or to be in the off-state such that the desired area of the nerve tissue within the spinal column is electrically stimulated. In addition, the amplitude, the pulse width, and the pulse rate of the respective stimulation signal applied on each of those implanted electrodes can be varied for a corresponding variation in area of excitation within the spinal column and in the intensity of excitation.

Deciding how to optimally provide electrical stimulation therapy to any particular individual involves three steps of screening. The first step of screening involves determining whether electrical stimulation of electrically excitable tissue can provide sufficient enough therapeutic effect to be worth implanting the electrodes near the electrically excitable tissue of the patient. The second step of screening involves adjusting the parameters of the respective stimulation signal applied on each of the implanted electrodes to optimize therapeutic effect before those electrodes are implanted for the long-term. The third step of screening involves readjusting the stimulation signal parameters for each of the stimulation electrodes that have been implanted for the long-term to continually optimize therapeutic effect.

In the prior art screening system and method, an array of electrodes is implanted temporarily near the electrically excitable tissue of a patient. Then, a clinician who is knowledgeable of the effects of electrical stimulation would vary the parameters of the respective stimulation signal applied on each of the implanted electrodes. The patient may rate the effectiveness in therapeutic effect for each variation in the parameters of the stimulation signals. If electrical stimulation of electrically excitable tissue does result in a sufficient enough therapeutic effect for the patient, then the electrodes are implanted for the long term with stimulation signals having parameters that lead to optimized therapeutic effect for the particular patient. In addition, by using radio-frequency telemetry with the implantable pulse generator, parameters of the stimulation signals can be adjusted to continually optimize therapeutic effect after the stimulation electrodes have been implanted permanently.

In the prior art screening system and method, the knowledgeable clinician with nonportable equipment performs the screening procedure. As stimulation signals with various parameter settings are applied on the electrodes, the clinician or patient records a rating of therapeutic effect. This procedure can be time-consuming and laborious because of the many possible combinations of parameter settings. U.S. Pat. No. 5,370,672 to Fowler et al. discloses a computer-controlled neurological stimulation system for automating the screening procedure to reduce the time and labor required during screening. However that system, which uses a computer terminal and a graphics drawing tablet, is non-portable and can be expensive.

Because of the non-portability of the prior art screening systems, the clinician and patient spend many hours in a clinical setting. Moreover, because of the non-portability of the prior art screening system, the rating of therapeutic effect under normal daily activities of the user are not available. Thus, a screening system, that is inexpensive and that is adapted to be portable, is desired.

OBJECTS OF THE INVENTION

Accordingly, a primary object of the present invention is to provide a screening device that is inexpensive and that is adapted to be portable for providing and recording therapeutic effect.

In particular, an object of the present invention is to implement a screening system and procedure whereby the user can carry the screening device during normal daily activities of the user. The user can easily adjust the parameters of the respective stimulation signal to be applied on each of at least one implanted electrode and can easily input a rating of therapeutic effect during normal daily activities of the user.

SUMMARY Of THE INVENTION

In a principal aspect, the present invention takes the form of a stimulation device for screening therapeutic effect on a living organism from electrical stimulation of a plurality of electrodes wherein at least one of the plurality of electrodes is implanted near electrically excitable tissue of the living organism. The user of this stimulation device inputs a selection of selected parameters of a respective stimulation signal to be applied on each of the plurality of electrodes via electrode configuration inputs on the device. In an advantageous feature, those inputs allow the user to select settings for the polarity, the pulse amplitude, the pulse width, and the pulse rate of the stimulation signals applied on each of the electrodes. Alternatively, the stimulation device automatically sets the stimulation signal parameters that historically have produced high ratings. A clinician would enter the stimulation signal parameters that have historically produced high ratings into a memory.

Alternately, or in addition, the stimulation device includes a "reset" function that allows the settings to return to a preset setting from whatever their current setting is. The preset setting may be either a setting preprogrammed by the physician or clinician or a level set by the patient through the patient's own selection of settings for polarity, pulse amplitude, pulse width or pulse rate.

Additionally, a control unit, operatively connected to the electrode configuration inputs, generates the control signals that control a signal generator that in turn generates the respective stimulation signal to be applied on each of the plurality of electrodes according to the parameters. Once those stimulation signals have been applied on the electrodes, the user can input a rating of the therapeutic effect from application of the respective stimulation signal on each of the plurality of electrodes.

A casing holds substantially all the components of the stimulation device. This casing is adapted to be portable with the user such that the user can carry the stimulation device during normal daily activities of the user. This embodiment of the present invention may be applied to particular advantage when the user can input the physical activity that corresponds to a rating thus further optimizing pain reduction by recording the variations in pain reduction for different physical activities.

In another aspect of the present invention, memory stores the selected parameters and the corresponding rating entered by the user for each set of selected parameters. Each of those ratings and the corresponding selected parameters that resulted in each of those ratings can be displayed on a display screen of the stimulation device. Alternatively, each of those ratings and the corresponding selected parameters that resulted in each of those ratings can be downloaded from the memory to a computer or a printer for further data analysis. Additionally, the present invention can optimize pain reduction by determining the selected parameters that resulted in a highest rating of all the ratings stored in memory.

These and other features and advantages of the present invention will be better understood by considering the following detailed description of the invention which is presented with the attached drawings.

DESCRIPTION OF THE PREFERRED EMBODIMENTS

Figure 1:
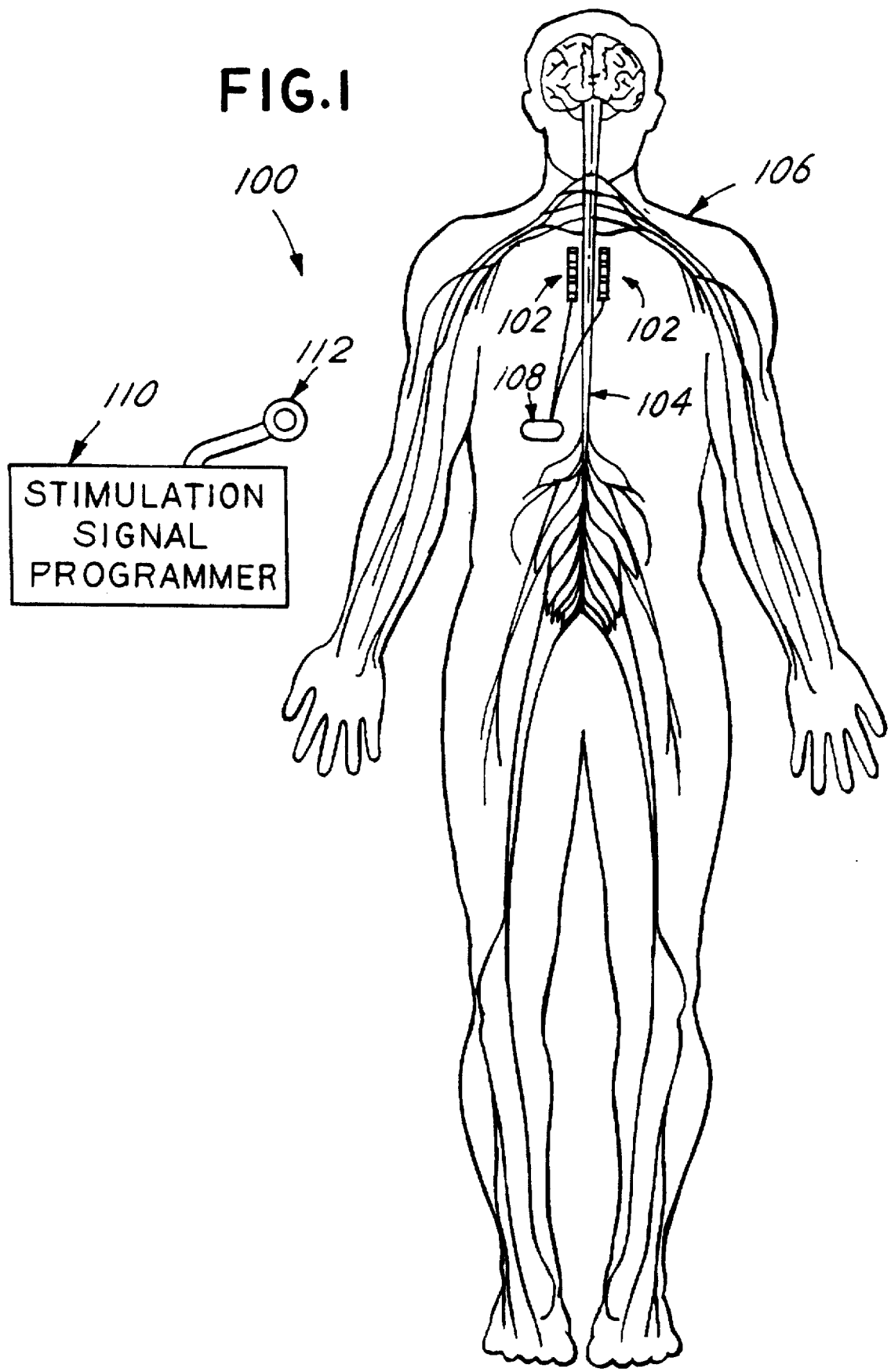
FIG. 1 shows a typical electrical stimulation system for reducing pain in a human body.

Referring to FIG. 1, an example electrical stimulation system 100 comprises leads 102 implanted near electrically excitable tissue 104 of a human body 106. Each lead has an array of at least one electrode. The electrically excitable tissue of FIG. 1 is any electrically excitable tissue including but not limited to nerve tissue wherever found in the body or muscle tissue. The electrical stimulation system of FIG. 1 also includes an implantable pulse generator 108 which provides the respective stimulation signal to each of the electrodes in the array of electrodes 102. The preferred embodiment of the present invention is described for the electrical stimulation system 100 used to achieve the therapeutic effect of reducing pain in the human body 106. However, it should be appreciated that the present invention can be used in any electrical stimulation system having implanted electrodes for achieving any therapeutic effect in any living organism.

A stimulation signal programmer 110 controls the implantable pulse generator 108 to generate respective stimulation signals having specified signal parameters for each of the electrodes in the array of electrodes 102. The stimulation signal programmer controls the pulse generator by direct connection to the pulse generator or by sending control signals via an antenna 112. An example of a directly connected pulse generator system is the Screener 3625 system available from Medtronic, Inc., Minneapolis, Minn. An example of a remotely controlled pulse generator system is the ITREL II system also available from Medtronic, Inc. While the preferred system employs fully implanted elements, systems employing an implanted receiver coupled by radio-frequency to an external power source may also be used in the practice of the present invention. Such systems are also available from Medtronic, Inc. under the trademarks X-trel and Mattrix.

Figure 2:
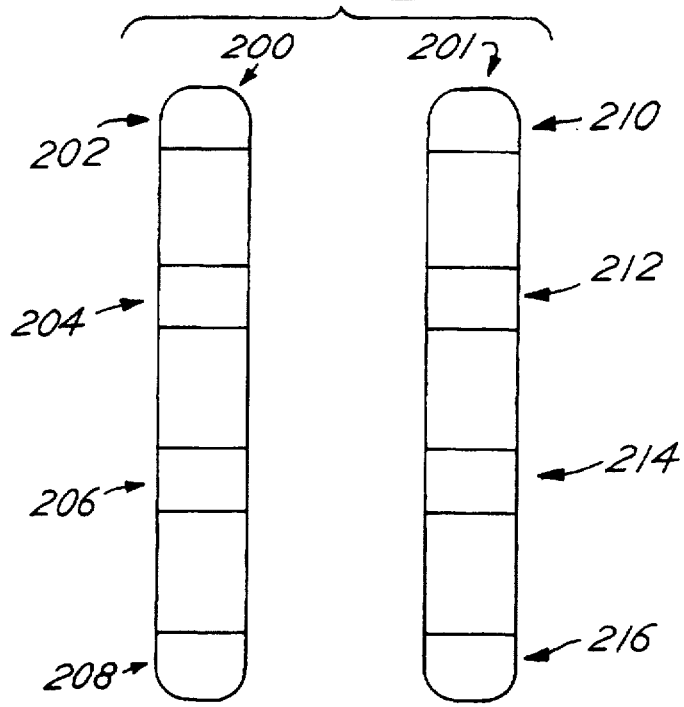
FIG. 2 is an enlarged illustration of the leads carrying stimulation electrodes implanted near electrically excitable tissue in the electrical stimulation system of FIG. 1.

FIG. 2 is an enlarged illustration of a first lead 200 carrying a first array of electrodes and a second lead 201 carrying a second array of electrodes implanted near electrically excitable tissue such as the leads 102 of FIG. 1. The first lead 200 includes a first electrode 202, a second electrode 204, a third electrode 206, and a fourth electrode 208. The second lead 201 includes a fifth electrode 210, a sixth electrode 212, a seventh electrode 214, and an eighth electrode 216. Within the electrical stimulation system of FIG. 1, the electrodes on the first lead may be operatively connected to a first channel of stimulation signal such that all of the electrodes on the first lead have the same source of stimulation signal applied thereon. Similarly, the electrodes on the second lead may be operatively connected to a second channel of stimulation signal such that all of the electrodes on the second lead have the same source of stimulation signal applied thereon.

In the electrical stimulation system 100 of FIG. 1, a can holding the implantable pulse generator 108 may also act as a stimulation electrode. Alternatively, a stimulation electrode may be disposed on the skin of the human body 106. For electrical stimulation of electrically excitable tissue 104, at least one stimulation electrode is implanted near the electrically excitable tissue 104.

Figure 3:
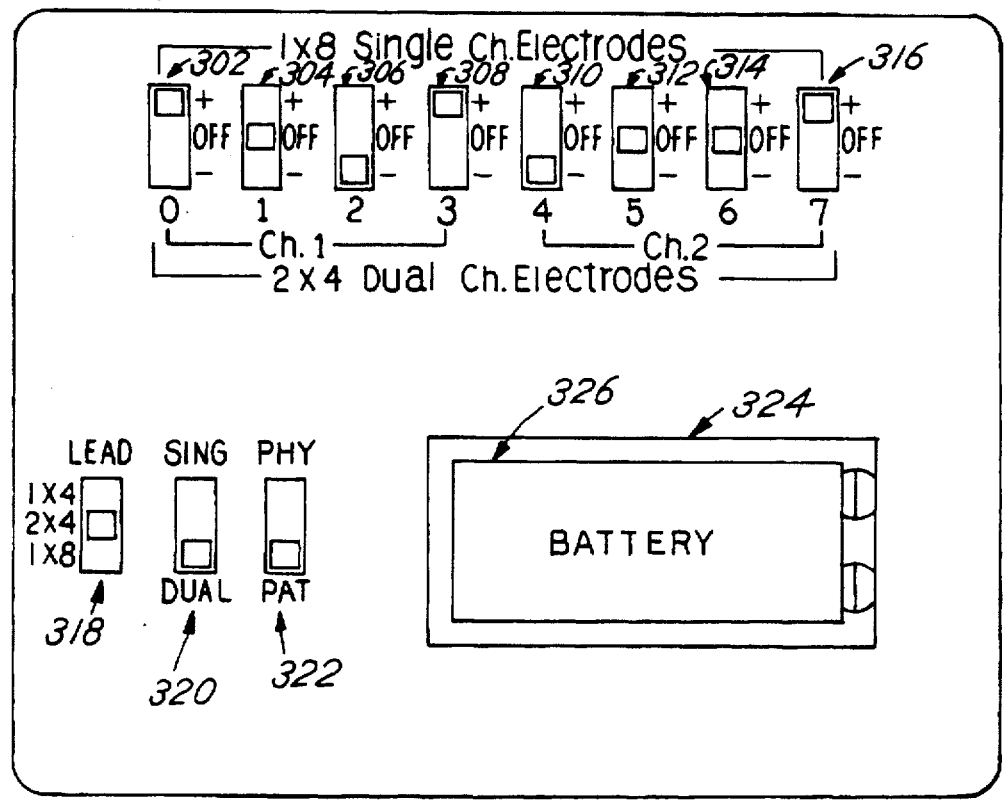
FIG. 3 shows the switches located on a first face of the stimulation device according to a preferred embodiment of the present invention.

FIG. 3 shows a first face 301 of the stimulation device 300 according to a preferred embodiment of the present invention. The polarity of each of the stimulation electrodes is first specified. The polarity for a stimulation electrode indicates whether a positive terminal of that pulse generator or a negative terminal of that pulse generator will be coupled to the stimulation electrode. If a positive polarity is chosen for a stimulation electrode, then the positive terminal of that pulse generator is operatively coupled to that stimulation electrode. Alternatively, if a negative polarity is chosen for a stimulation electrode, then the negative terminal of that pulse generator is operatively coupled to that stimulation electrode. In addition, a stimulation electrode can be configured to be in the off-state whereby no stimulation signal would be applied on the electrode with the electrode simply providing a high impedance.

The configuration of polarities for each of the electrodes determines the location and area of excitation within the electrically excitable tissue which in turn determines the location and area of pain reduction in another part of the body. Thus, an important and critical step in the screening procedure is to determine the respective polarity of the stimulation signal for each electrode. In screening, a clinician determines whether an electrical stimulation system should be implanted in a patient for the long term, and if so, what respective stimulation signal should be applied on each of the implanted electrodes for optimum therapeutic effect. A first important step in that screening process is to try different polarity combinations.

Thus, the first face 301 of the stimulation device 300 of FIG. 3 shows three-input-to-one-output switches for specifying the respective polarity for each of the stimulation electrodes. For example, if the array of electrodes 200 of FIG. 2 were coupled to the stimulation device 300 of FIG. 3, then each three-input-to-one-output switch sets the polarity for a respective stimulation electrode in FIG. 2. Referring to FIGS. 2 and 3, a first switch 302 sets the polarity of the first electrode 202, a second switch 304 sets the polarity of the second electrode 204, a third switch 306 sets the polarity of the third electrode 206, a fourth switch 308 sets the polarity of the fourth electrode 208, a fifth switch 310 sets the polarity of the fifth electrode 210, a sixth switch 312 sets the polarity of the sixth electrode 212, a seventh switch 314 sets the polarity of the seventh electrode 214, and an eighth switch 316 sets the polarity of the eighth electrode 216. Note that each switch can be toggled to "+" for a positive polarity, "−" for a negative polarity, or to "off" for an off-state polarity. Additionally, note that another switch may be provided to specify the polarity of the can holding the implantable pulse generator 108.

A variety of polarity configuration combinations are possible for the stimulation electrodes. Note that since there are three possible polarities for each stimulation electrode, and there are nine stimulation electrodes (including the eight stimulation electrodes on the leads 102 and one stimulation electrode via the can of the implantable pulse generator), there are $3^9$ possible polarity configuration combinations possible. However, the polarity configuration that can cause electrical stimulation of the tissue creates a potential difference between any of the two electrodes. Thus, the combination of a respective polarity for each of the electrodes has a potential difference between at least two of the implanted electrodes in order to cause electrical stimulation of electrically excitable tissue and thus in order to cause a therapeutic effect.

Another three-input-to-one-output switch 318 specifies the type of leads carrying the electrodes. For example, the leads of electrodes 200 and 201 of FIG. 2 are a 2×4 combination (two leads, each with four electrodes). Alternatively, the stimulation device can use a 1×8 combination (one lead with eight electrodes) or a 1×4 combination (one lead with four electrodes).

A two-input-to-one-output switch 320 allows the user to toggle between "SING" for single channel excitation and "DUAL" for dual channel excitation. For example, in the leads of electrodes 200 and 201 of FIG. 2, if switch 320 were toggled to "SING" then all eight electrodes would have a respective stimulation signal originating from the same one single channel source. Each electrode can have either a positive, negative, or off-state polarity of the signal from that one single channel source.

Alternatively, if switch 320 were toggled to "DUAL" then two channels of stimulation signals would be available. For example, in the leads of electrodes 200 and 201 of FIG. 2, the first, second, third, and fourth electrodes 202, 204, 206, and 208 respectively may have a respective stimulation signal originating from a first channel source. Each of those electrodes can have either a positive, negative, or off-state polarity of the signal from that first channel source as the first, second, third, and fourth switches 302, 304, 306 and 308 respectively set the polarity of those electrodes.

Similarly, the fifth, sixth, seventh, and eighth electrodes 210, 212, 214, and 216 respectively may have a respective stimulation signal originating from a second channel source. Each of those electrodes can have either a positive, negative, or off-state polarity of the signal from that second channel as the fifth, sixth, seventh, and eighth switches 310, 312, 314, and 316 respectively set the polarity of those electrodes.

Another two-input-to-one-output switch 322 allows the user to put the stimulation device in one of a "PHY" for physician mode and a "PAT" for patient mode. Changing the polarity of the stimulation signal applied on any electrode can have a dramatic effect on the therapeutic effect from electrical excitation of tissue. Thus, the polarity of the stimulation signal applied on each of the electrodes via switches 302–316 can be set up to be changed only when switch 322 is set in the physician mode.

When switch 322 is in patient mode, the patient-user may be able to adjust other parameters of the stimulation signals only such as the pulse amplitude, the pulse width, or pulse rate of the stimulation signals applied on the electrodes. To ensure that a patient cannot toggle with the switches 302–316 for changing the polarity of any individual electrode, the stimulation device can be locked into patient mode once the device has been set to patient mode, by requiring a password to toggle back to the physician mode. This password requirement ensures that only a knowledgeable clinician or physician can adjust the polarity of the signal applied on individual electrodes via switches 302–316.

Finally, the first face 301 of the stimulation device 300 of FIG. 3 has a battery compartment 324 for holding a battery 326. By including a battery, the stimulation device of the present invention is portable since the stimulation device is battery powered. Because the user can carry the stimulation device during normal daily activities of the user, the screening process can take place predominantly outside of a clinical setting, providing more flexibility to the user. Moreover, portability results in more accurate screening because the user can assess the therapeutic effects of the electrical stimulation therapy during normal daily activities of the user.

Figure 4:
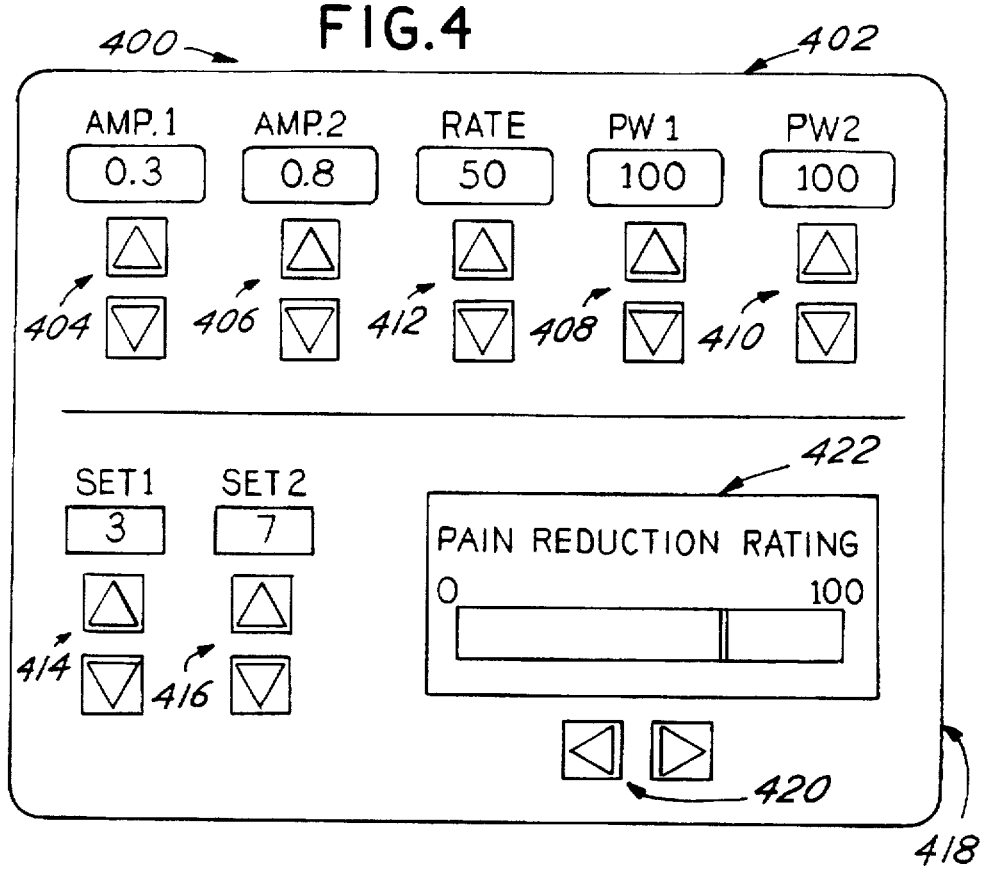
FIG. 4 shows the buttons located on a second face of the stimulation device according to a preferred embodiment of the present invention when the device is in patient mode.

FIG. 4 shows a second face 402 of the stimulation device 400 according to a preferred embodiment of the present invention. The second face includes scrolling buttons that are electrode configuration inputs that the user can use to specify parameters of the respective stimulation signal applied on each of the electrodes.

A first set of amplitude scrolling buttons 404 allows the user to scroll through possible amplitudes for the stimulation signal supplied by a first channel of a signal generator. A second set of amplitude scrolling buttons 406 allows the user to scroll through possible amplitudes for the stimulation signal supplied by a second channel of the signal generator. The user can select the amplitude setting for the respective stimulation signal applied on each of the implanted electrodes via these amplitude scrolling buttons. In the stimulation device 400 of FIG. 4, the amplitude of the signal from the first channel is set at 0.3 V, and the amplitude of the signal from the second channel is set at 0.8 V by the user. Alternatively, the amplitude of the signals applied on the stimulation electrodes can also be set in terms of a current magnitude in amperes instead of in voltages.

A first set of pulse width scrolling buttons 408 allows the user to scroll through possible pulse widths for the stimulation signal supplied by a first channel of a signal generator. A second set of pulse width scrolling buttons 410 allows the user to scroll through possible pulse widths for the stimulation signal supplied by a second channel of the signal generator. The user can select the pulse width for the respective stimulation signal applied on each of the implanted electrodes via these pulse width scrolling buttons. In the stimulation device 400 of FIG. 4, the pulse width of the signal from the first channel is set at 100 µs, and the pulse width of the signal from the second channel is also set at 100 µs by the user.

A set of pulse rate scrolling buttons 412 allows the user to scroll through possible pulse rates for the stimulation signals applied on the implanted electrodes. The user can then select the pulse rate for the respective stimulation signal applied on each of the implanted electrodes via these pulse rate scrolling buttons. In the stimulation device 400 of FIG. 4, the pulse rate is set by the user at 50 cycles/second for the stimulation signal applied on all of the implanted electrodes. Alternatively, a respective set of pulse rate scrolling buttons can be provided for each implanted electrode such that a respective pulse rate can be specified for each respective stimulation signal applied on each of the implanted electrodes.

A first set of setting scrolling buttons 414 allows the user to scroll through preset polarity configurations for electrodes operatively coupled to a first channel of a signal generator. A second set of setting scrolling buttons 416 allows the user to scroll through preset polarity configurations for electrodes operatively coupled to a second channel of the signal generator.

For n-number of electrodes and three possible polarities for each electrode, there would be $3^n$ possible number of combinations of polarity configurations for the n electrodes. Thus, for the eight electrodes of FIG. 2, there are more than 6,000 possible combinations of polarity configurations. However, clinical results show that approximately ten configurations can sufficiently reduce pain in approximately 80% of the patients who decide to get an electrode implant for pain-reduction therapy. The setting scrolling buttons 414 and 416 allow the user to try those ten configurations first by automatically configuring the electrodes to have the polarity of those ten commonly used configurations.

Alternatively, when switch 322 of FIG. 3 is set in "PHY" for physician mode, the polarity configurations, that can be selected via the setting scrolling buttons 414 and 416, can be programmed into the memory of the stimulation device 400 by a physician or clinician. Those automatically selected electrode configurations may be those that have historically resulted in high ratings of therapeutic effect for a group of similarly situated patients or may be other electrode configurations set as the physician or clinician dictates. In addition, the parameters may also be preset by the physician or clinician to the settings that have historically resulted in the highest ratings of therapeutic effect for a group of similarly situated patients or may be other parameters set as the physician or clinician dictates.

In another alternate embodiment, the automatically selected electrode configurations may be those that have historically resulted in a high rating of therapeutic effect for the particular user-patient. These particular electrode configurations may be determined by the physician or clinician. As above, parameters may be preset by the physician or clinician according either to settings that have historically resulted in high ratings of therapeutic effect for a group of similarly situated patients or that have historically resulted in high ratings for the particular user-patient. These historical settings for the particular user-patient may be changed by the patient as the patient scrolls through inputs to change the parameters as will be described hereafter. This feature of the invention may be beneficial by allowing the user-patient to determine the parameters for a particular electrode setting that has resulted in a high therapeutic rating in the past.

In a further alternate embodiment, the device may be "reset" to a particular parameter configuration from whatever the current parameter settings are. This may be accomplished by either pushing a separate "reset" button or by pushing a particular combination of buttons simultaneously. In either case, the device detects the "reset" condition by detecting the pushing the "reset" button or the pushing of the particular combination of buttons simultaneously predetermined to be a "reset" request. Upon receiving a "reset" request, the device returns all or some of the electrode parameters to a predetermined setting that has previously been stored in memory. The predetermined setting may be, as set out above, either a physician or clinician determined setting or a setting determined by the patient. This "reset" feature of the invention may be beneficial by allowing the user-patient to easily return to a set of predetermined electrode parameters when, as described below, the patient has changed a number of parameters from their initial settings.

Referring to FIGS. 2 and 4, the first set of setting scrolling buttons 414 allows the user to scroll through those preset polarity configurations for the first lead 200 of electrodes including the first, second, third, and fourth electrodes, 202, 204, 206, and 208 respectively. The second set of setting scrolling buttons 416 allows the user to scroll through those preset polarity configurations for the second lead of electrodes including the fifth, sixth, seventh, and eighth electrodes, 210, 212, 214, and 216 respectively.

Two sets of setting scrolling buttons are provided because the pain reduction effect from electrical stimulation signals being applied on each lead of electrodes is additive. Thus, the user may first find the optimum polarity configuration for the first lead of electrodes by scrolling through the first set of setting scrolling buttons 414. Once the polarity configuration for the first lead of electrodes is then fixed on the optimum polarity configuration, the user may then find the optimum polarity configuration for the second lead of electrodes by scrolling through the second set of setting scrolling buttons 416. In FIG. 4, the user has chosen a polarity configuration numbered "3" via the first set of setting scrolling buttons for the first lead of electrodes and a polarity configuration numbered "7" via the second set of setting scrolling buttons for the second lead of electrodes.

The electrode configuration scrolling buttons are electrode configuration inputs. The pulse width scrolling buttons, the pulse rate scrolling buttons and the amplitude scrolling buttons are collectively referred to as parameter scrolling buttons. These parameter scrolling buttons allow the user to select parameters of pulse width, pulse rate and amplitude of a stimulation signal to be applied to the electrode configuration determined by the electrode configuration scrolling button. The parameter scrolling buttons allow the user to easily adjust these parameters of the stimulation signals to find the optimum set of parameters for pain reduction. Alternatively, any of the scrolling button inputs can be implemented by means well known in the art, including but not limited to, dials or mechanical sliding bars.

Once a set of parameters for the stimulation signals has been selected, and the respective stimulation signal with those parameters have been applied on each of the electrodes, the user inputs a rating of the pain reduction corresponding to those stimulation signals via a set of rating scrolling buttons 420. A display screen 422 shows the possible ratings from 0 to 100 with 0 being a lowest possible score for a lowest possible rating of pain reduction and with 100 being the highest possible score for a highest possible rating of pain reduction.

This rating can include a rating of both the area of coverage of reduced pain and the level of pain reduction for a given area. The rating scrolling buttons 420 allow the user to scroll through the possible ratings, for example of 0–100 in increments of 1, and to select one of the ratings for a corresponding set of parameters of the stimulation signals. Alternatively, as above, the rating scrolling input can be implemented by means well known in the art.

A casing 418 of the stimulation device 400 of FIG. 4 is adapted to be portable as shown by the first face of the stimulation device in FIG. 3. Thus, the user can easily carry around the stimulation device of the present invention during normal daily activities. The stimulation device can be put inside a pocket, or can be attached to a key chain, or can be attached to a belt. In any case, to ensure that the parameter settings via the scrolling buttons are not inadvertently changed by inadvertently depressing one of those buttons, the stimulation device may come with a transparent cover over the first and second faces. These covers can be lifted up to use the switches and scrolling buttons when adjusting the parameters of the stimulation signals, and can be placed over the switches and buttons when the stimulation device is being carried around by the user.

This portability feature of the stimulation device can advantageously result in more accurate screening because the user can carry the stimulation device around during normal daily activities and can account for the variation in pain reduction with a variety of daily activities. For example, for a given set of selected stimulation signal parameters, the rating of pain reduction may vary from when the user is lying down to when the user is running.

Figure 5:
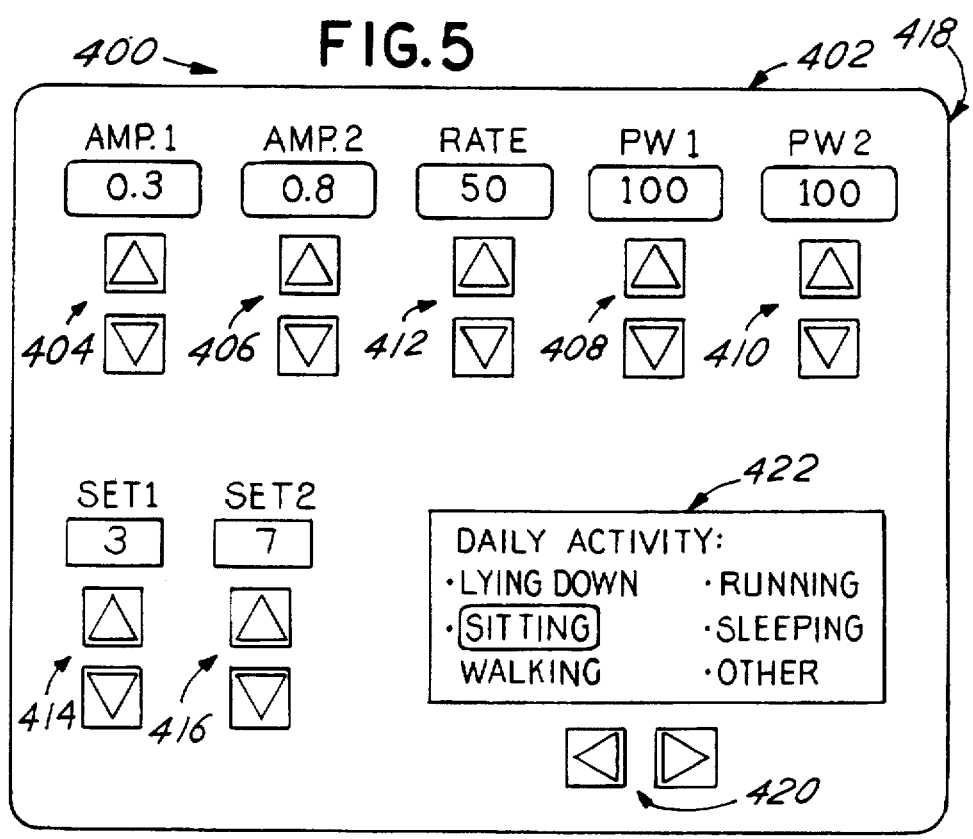
FIG. 5 shows the second face of the stimulation device of FIG. 4 with the display screen on that face showing possible daily activities of the user.

FIG. 5 shows the stimulation device 400 of FIG. 4 where similar elements in FIGS. 4 and 5 have the same number label. The display screen 422 in FIG. 5 however is used to show possible daily activities. The rating scrolling buttons 420 may be used as a physical activity input whereby the user can scroll through different possible daily activities to select the physical activity for a given rating. In the stimulation device of FIG. 5, the possible daily activities may be "Lying Down", "Sitting", "Walking", "Running", "Sleeping", or "Other"; the user in this case has selected "Sitting".

In this manner, pain can be further minimized because the stimulation signal parameters can be adjusted to accommodate all possible daily activities. In contrast, the prior art electrical stimulation screening system and method was not portable, and the patient was confined to a clinical setting during the screening process. Because of the expensive instrumentation and equipment used in the prior art system, the instrumentation and equipment was reused for a large number of patients. The stimulation device of the present invention can be manufactured inexpensively, and each patient can carry home such a stimulation device for screening during normal daily activities.

Referring to the first face 301 of the stimulation device 400 of the present invention, switch 322 is set at "PAT" for patient mode when the patient-user inputs the stimulation signal parameters via the scrolling buttons. Once the patient-user has tried a sufficient number of various parameters and has entered in the respective rating for each set of those selected parameters, the patient-user returns the stimulation device to the clinician or physician. Switch 322 is then set at "PHY" for physician mode. All of the sets of selected parameters and a respective rating for each set of the selected parameters has been stored in memory.

Figure 6:
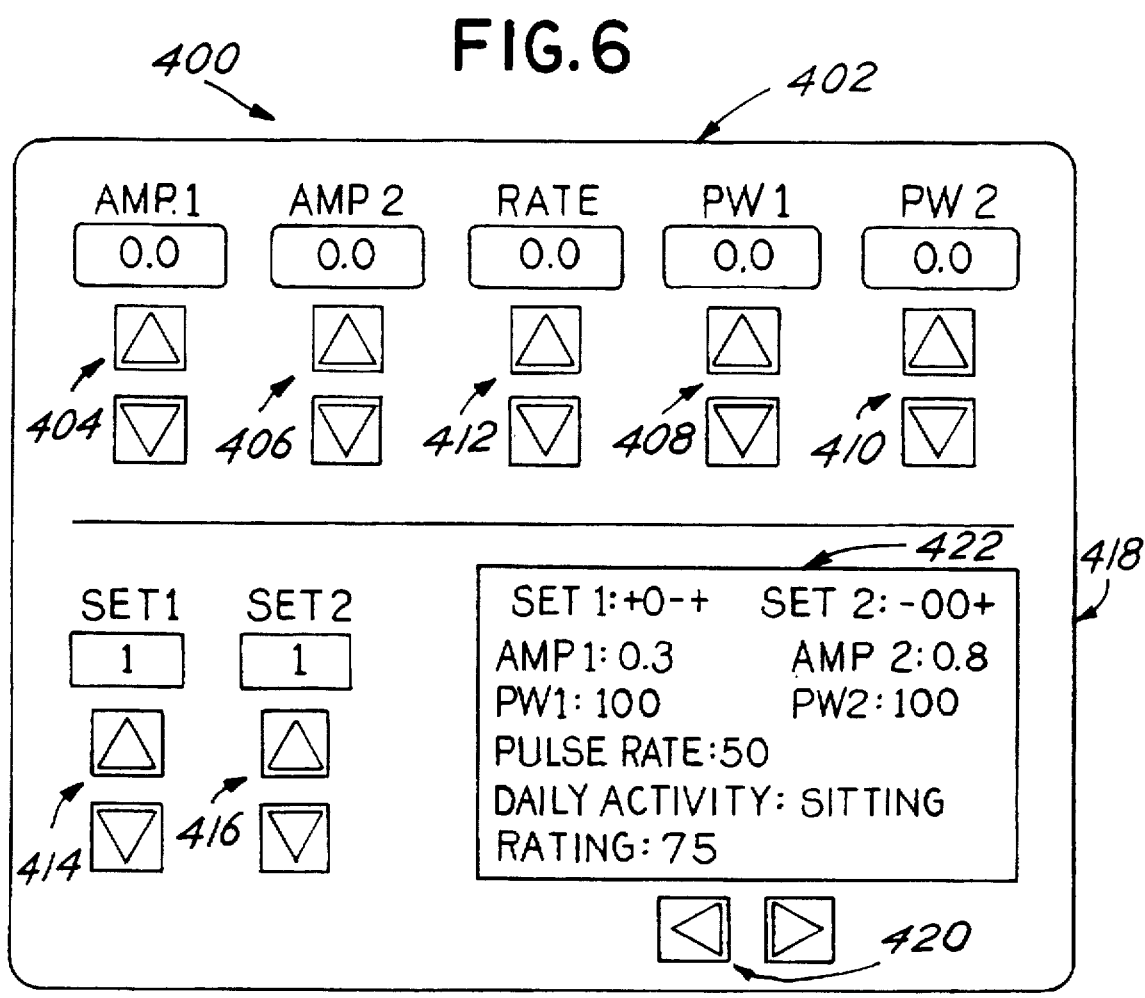
FIG. 6 shows the display screen contents of the second face of the stimulation device of FIG. 4 when the device is in physician mode.

FIG. 6 shows the stimulation device 400 of FIG. 4 where similar elements in FIG. 4 and 6 have the same number label. However, switch 322 in the stimulation device of FIG. 6 has been set in physician mode, and display screen 422 shows each set of selected parameters and the respective rating for each set of selected parameters.

In the display screen 422 of FIG. 6, one set of stimulation signal parameters are shown. If the first and second leads 200 and 201 of FIG. 2 were used with this stimulation device and if the first lead of electrodes were operatively coupled to a first channel of a stimulation signal generator and if the second lead of electrodes were operatively coupled to a second channel of a stimulation signal generator, then the polarity on the first, second, third, and fourth electrodes 202, 204, 206, and 208 respectively were configured to have positive, off-state, negative, and positive polarities respectively. The polarity on the fifth, sixth, seventh, and eight electrodes 210, 212, 214, and 216 respectively were configured to have negative, off-state, off-state, and positive polarities respectively.

The amplitude of the stimulation signals applied on the first lead of electrodes was 0.3 V and on the second lead of electrodes was 0.8 V. The pulse width of the stimulation signals applied on all of the electrodes was 100 µs, and the pulse rate of the stimulation signal applied on all of the electrodes was 50 cycles/second. The patient-user entered a rating of 75 for pain-reduction with those stimulation signal parameters, and the user had been sitting during application of those stimulation signals.

The clinician or physician can scroll through all of the sets of selected parameters and corresponding ratings. Alternatively, the stimulation device of the present invention can include a microprocessor that can rank the sets of selected parameters according to the level of rating to determine optimum selected parameters that produced a highest rating of all ratings stored in memory. In an alternative embodiment, the data of selected parameters and corresponding ratings stored in memory can be downloaded to a computer or a printer for further data analysis.

Figure 7:
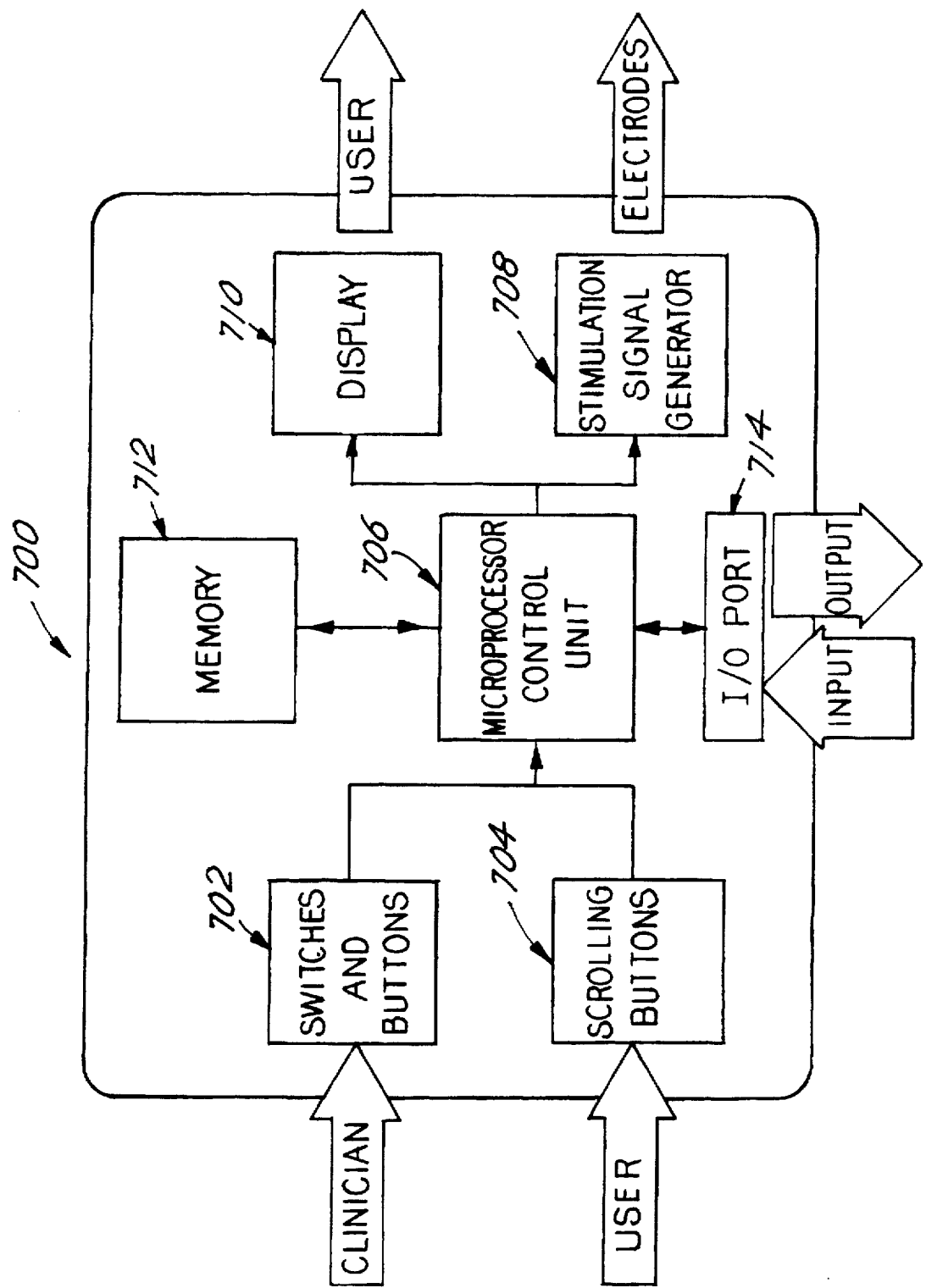
FIG. 7 shows a block diagram of components inside the stimulation device of FIGS. 3–6.

FIG. 7 shows a block diagram of components that are inside the stimulation device 700 of the present invention. Referring to FIG. 7, the stimulation device comprises electrode configuration inputs which includes switches 702 and scrolling buttons 704. The clinician or user would select the polarity configuration of the implanted electrodes or the parameters of the respective signal for each of the implanted electrodes via those electrode configuration inputs. A microprocessor control unit 706 sends control signals to a stimulation signal generator 708 to generate the stimulation signals having these selected parameters. A display 710 shows ratings and sets of the selected parameters with their corresponding ratings. A memory 712 stores those sets of selected parameters with their corresponding ratings as the user tries a series of selected parameters.

The microprocessor control unit 706 can store into memory 712 the preselected parameters for each of the electrodes entered by a clinician via the input of the I/O (Input/Output) port 714. Alternatively, the preselected parameters can be sent to the memory 712 from another computer via the input of the I/O port 714. The microprocessor control unit can also read out of memory the selected parameters and the corresponding rating for each of those selected parameters via the output of the I/C port 714 such that data can be downloaded to a computer or a printer for further data analysis.

Figure 8:
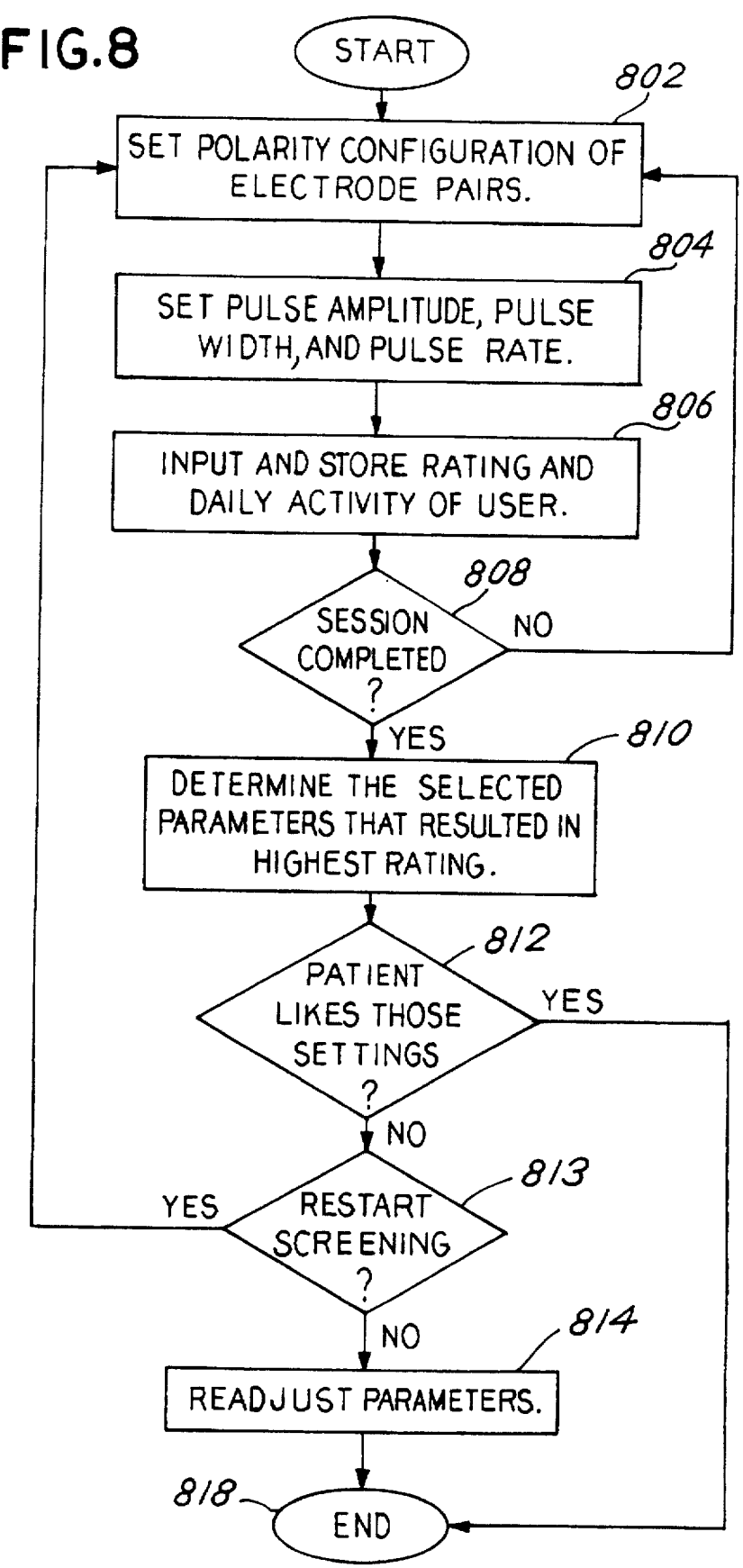
FIG. 8 shows a flowchart of the steps that are performed during a screening session using the stimulation device of the present invention.

FIG. 8 shows a flowchart of typical steps in the screening procedure of the present invention. The respective polarity of each of the implanted electrodes is configured at step 802. Then selected parameters of a respective amplitude, a respective pulse width, and a respective pulse rate are also set for each of the implanted electrodes at step 804. Then the user makes an assessment of the therapeutic effect from those selected parameters and inputs a rating and a daily activity the user has been engaged in for that rating in step 806. The selected parameters and their corresponding ratings are stored in memory.

The user then makes a decision as to whether to end the session when enough sets of selected parameters has been tried at step 808. If the user wants to try more selected parameters, the user returns to step 802. If the user has completed trying various sets of selected parameters, then the stimulation device of the present invention with the microprocessor 706 of FIG. 7 determines the optimal selected parameters that resulted in a highest rating of all ratings stored in memory 712 in FIG. 7 at step 810.

The optimum selected parameters are tried once again to ensure that the patient does like the therapeutic effects from those optimum selected parameters in step 812. If the patient does like those parameters for therapeutic effect, then the screening process ends by going to the end step 818. If the patient does not like those optimum selected parameters for therapeutic effect, then the parameters can be readjusted slightly until the patient likes the level of therapeutic effect at step 814 or the screening process can be completely restarted back at step 802 until the patient can choose different optimum selected parameters. Alternately, the user-patient can activate the "reset" process 816 described above to return to preselected parameters. The program then proceeds to the end step 818.

In this manner, a screening system, that is adapted to be portable and that is easy to use and is relatively inexpensive, can be provided. Thus, the patient-user can adjust the parameters of the respective stimulation signal that is applied on each of the implanted electrodes outside of a clinical setting and during normal daily activities of the user. Consequently, the user can more easily and more accurately find an optimum set of stimulation signal parameters that can reduce pain for the patient throughout normal daily activities of the user.

The advantages of the invention described herein can be generalized to any number of implanted electrodes and any combination of stimulation signal channels for any of those electrodes. Moreover, the invention can be generalized to any number of electrodes for any scrolling button that is used to set the parameters of the signals applied on those electrodes. More importantly, the present invention can be generalized for use with any medical device that includes implanted electrodes for inducing any therapeutic effect in any living organism by electrical stimulation of any electrically excitable tissue. Neural tissue is one example of electrically excitable tissue and includes brain tissue and peripheral nerve tissue in addition to nerve tissue within the spinal cord. Accordingly, the forgoing description is by way of example only. The invention is limited only as defined in the following claims and equivalents thereof.

We claim:

1. A portable stimulation screening device for screening, during normal activities of a patient user, therapeutic effect on said patient user from electrical stimulation by at least one electrode implanted near electrically excitable tissue of said patient user, said stimulation device comprising:

a signal generator coupled to said at least one electrode;

means for inputting a set of selected parameters that define a respective stimulation signal to be applied on each of said at least one electrode, said set of selected parameters being selected by said patient user;

a control unit, operatively coupled to said signal generator and to said means for inputting said set of selected parameters, for controlling said signal generator to generate said respective stimulation signal, having said set of selected parameters, to be applied on each of said at least one electrode;

means for inputting a corresponding rating of therapeutic effect entered by said patient user for said set of selected parameters, said therapeutic effect resulting from application of said respective stimulation signal, having said set of selected parameters, on each of said at least one electrode; and a casing that holds components of said portable stimulation screening device and that is adapted to be portable with said patient user such that said patient user carries said portable stimulation screening device and screens said therapeutic effect during normal activities of said patient user.

2. The portable stimulation screening device of claim 1, further comprising:

means for inputting a corresponding normal activity as entered by said patient user, said corresponding normal activity corresponding to said set of selected parameters and said corresponding rating of therapeutic effect.

3. The portable stimulation screening device of claim 1, wherein said casing includes a battery compartment and a battery in said battery compartment, said battery being coupled to the components of said portable stimulation screening device such that said portable stimulation screening device is battery powered.

4. The portable stimulation screening device of claim 1, wherein said means for inputting said set of selected parameters includes:

a respective three input to one output switch, for each of said at least one electrode, each of said three inputs corresponding to a respective one of a positive polarity, a negative polarity, and an off-state polarity of a voltage signal generated by said signal generator, wherein said patient user selects one of said three inputs to select a respective polarity of said voltage signal applied on each of said at least one electrode.

5. The portable stimulation screening device of claim 1, wherein said means for inputting said set of selected parameters includes:

means for allowing said patient user to select preset parameters as said set of selected parameters.

6. The portable stimulation screening device of claim 5, wherein said preset parameters have historically resulted in high ratings of therapeutic effect for a large number of patients.

7. The portable stimulation screening device of claim 5, wherein said preset parameters have historically resulted in high ratings of therapeutic effect for said patient user.

8. The portable stimulation screening device of claim 1, wherein said means for inputting said set of selected parameters includes:

means for inputting a respective amplitude of the respective stimulation signal for each of said at least one electrode, said respective amplitude being selected by said patient user.

9. The portable stimulation screening device of claim 1, wherein said means for inputting said set of selected parameters includes:

means for inputting a respective pulse width of the respective stimulation signal for each of said at least one electrode, said respective pulse width being selected by said patient user.

10. The portable stimulation screening device of claim 1, wherein said means for inputting said set of selected parameters includes:

means for inputting a respective pulse rate of the respective stimulation signal for each of said at least one electrode, said respective pulse rate being selected by said patient user.

11. The portable stimulation screening device of claim 1, wherein said control unit includes:

means for controlling the signal generator to generate the respective stimulation signal having a predetermined set of parameters for each of said at least one electrode when said patient user resets said portable stimulation screening device.

12. The portable stimulation screening device of claim 1, further comprising:

a memory for storing said set of selected parameters and said corresponding rating of therapeutic effect corresponding to said set of selected parameters.

13. The portable stimulation screening device of claim 12, further comprising:

means for determining an optimum set of selected parameters that produced a highest rating of therapeutic effect from all ratings of therapeutic effect stored in said memory.

14. The portable stimulation screening device of claim 1, further comprising:

a display screen for displaying said set of selected parameters and said corresponding rating of therapeutic effect corresponding to said set of selected parameters.

15. The portable stimulation screening device of claim 1, wherein said means for inputting a corresponding rating of therapeutic effect includes:

rating scrolling buttons for allowing said user to scroll through a list of ratings to select said corresponding rating of therapeutic effect from said list of ratings.

16. A portable stimulation screening device for screening, during normal activities of a patient user, therapeutic effect on said patient user from electrical stimulation by at least one electrode implanted near electrically excitable tissue of said patient user, said stimulation device comprising:

a signal generator coupled to said at least one electrode;

means for inputting a set of selected parameters that define a respective stimulation signal to be applied on each of said at least one electrode, said set of selected parameters being selected by said patient user, said means for inputting said set of selected parameters further comprising:

a respective three input to one output switch, for each of said at least one electrode, each of said three inputs corresponding to a respective one of a positive polarity, a negative polarity, and an off-state polarity of a voltage signal generated by said signal generator, wherein said patient user selects one of said three inputs to select a respective polarity of said voltage signal applied on each of said at least one electrode;

means for allowing said patient user to select preset parameters as said set of selected parameters;

means for inputting a respective amplitude of the respective stimulation signal for each of said at least one electrode, said respective amplitude being selected by said patient user;

means for inputting a respective pulse width of the respective stimulation signal for each of said at least one electrode, said respective pulse width being selected by said patient user; and means for inputting a respective pulse rate of the respective stimulation signal for each of said at least one electrode, said respective pulse rate being selected by said patient user;

a control unit, operatively coupled to said signal generator and to said means for inputting said set of selected parameters, for controlling said signal generator to generate said respective stimulation signal, having said set of selected parameters, to be applied on each of said at least one electrode, said control unit further including:

means for controlling the signal generator to generate the respective stimulation signal having a predetermined set of parameters for each of said at least one electrode when said patient user resets said portable stimulation screening device;

means for inputting a corresponding rating of therapeutic effect entered by said patient user for said set of selected parameters, said therapeutic effect resulting from application of said respective stimulation signal, having said set of selected parameters, on each of said at least one electrode, said means for inputting a corresponding rating of therapeutic effect further including:

rating scrolling buttons for allowing said user to scroll through a list of ratings to select said corresponding rating of therapeutic effect from said list of ratings;

a casing that holds components of said portable stimulation screening device and that is adapted to be portable with said patient user such that said patient user carries said portable stimulation screening device and screens said therapeutic effect during normal activities of said patient user, wherein said casing includes a battery compartment and a battery in said battery compartment, said battery being coupled to the components of said portable stimulation screening device such that said portable stimulation screening device is battery powered;

means for inputting a corresponding normal activity as entered by said patient user, said corresponding normal activity corresponding to said set of selected parameters and to said corresponding rating of therapeutic effect;

a memory for storing said set of selected parameters, said corresponding normal activity, and said corresponding rating of therapeutic effect corresponding to said set of selected parameters;

means for determining an optimum set of selected parameters that produced a highest rating of therapeutic effect from all ratings of therapeutic effect stored in said memory; and a display screen for displaying said set of selected parameters, said corresponding normal activity, and said corresponding rating of therapeutic effect for said set of selected parameters.

17. A method for screening, during normal activities of a patient user, therapeutic effect on said patient user from electrical stimulation by at least one electrode implanted near electrically excitable tissue of said patient user, said method including the steps of:

A. inputting a set of selected parameters that define a respective stimulation signal to be applied on each of said at least one electrode, said set of selected parameters being selected by said patient user;

B. generating and-applying said respective stimulation signal, having said set of selected parameters, on each of said at least one electrode;

C. inputting a corresponding rating of therapeutic effect as entered by said patient user for said set of selected parameters, said therapeutic effect resulting from application of said respective stimulation signal, having said set of selected parameters, on each of said at least one electrode; and D. inputting a corresponding normal activity as entered by said patient user, said corresponding normal activity corresponding to said set of selected parameters and said corresponding rating of therapeutic effect.

18. The method of claim 17, wherein said step B further includes the step of:

configuring each of said plurality of electrodes to have a respective one of a positive polarity, a negative polarity, and an off-state polarity as selected by said patient user.

19. The method of claim 17, wherein said step A further includes the step of:

inputting a respective amplitude of the respective stimulation signal for each of said at least one electrode, said respective amplitude being selected by said patient user.

20. The method of claim 17, wherein said step A further includes the step of:

inputting a respective pulse width of the respective stimulation signal for each of said at least one electrode, said respective pulse width being selected by said patient user.

21. The method of claim 17, wherein said step A further includes the step of:

inputting a respective pulse rate of the respective stimulation signal for each of said at least one electrode, said respective pulse rate being selected by said patient user.

22. The method of claim 17, wherein said step B further includes the step of:

generating and applying said respective stimulation signal, having preset parameters as said set of selected parameters, on each of said at least one electrode when said patient user selects said preset parameters as said set of selected parameters.

23. The method of claim 22, wherein said preset parameters have historically resulted in high ratings of therapeutic effect for a large number of patients.

24. The method of claim 22, wherein said preset parameters have historically resulted in high ratings of therapeutic effect for said patient user.

25. The method of claim 17, wherein said step B further includes the step of:

generating and applying the respective stimulation signal having a predetermined set of parameters on each of said at least one electrode when said patient user resets said set of selected parameters.

26. The method of claim 17, further including the step of:

storing into memory said set of selected parameters, said corresponding rating of therapeutic effect, and said corresponding normal activity.

27. The method of claim 26, further including the step of:

determining an optimum set of selected parameters that produced a highest rating of therapeutic effect across a variety of normal activities for said patient user from all ratings of therapeutic effect stored in said memory.

28. The method of claim 26, further including the step of:

downloading said set of selected parameters, said corresponding rating of therapeutic effect, and said corresponding normal activity from said memory to a selected one of a computer and a printer.

29. The method of claim 17, further including the step of:

displaying on a screen said set of selected parameters, said corresponding rating of therapeutic effect, and said corresponding normal activity.

30. A method for screening, during normal activities of a patient user, therapeutic effect on said patient user from electrical stimulation by at least one electrode implanted near electrically excitable tissue of said patient user, said method including the steps of:

A. inputting a set of selected parameters that define a respective stimulation signal to be applied on each of said at least one electrode, said set of selected parameters being selected by said patient user, said step A further including the steps of:

inputting a respective amplitude of the respective stimulation signal for each of said at least one electrode, said respective amplitude being selected by said patient user;

inputting a respective pulse width of the respective stimulation signal for each of said at least one electrode, said respective pulse width being selected by said patient user; and inputting a respective pulse rate of the respective stimulation signal for each of said at least one electrode, said respective pulse rate being selected by said patient user;

B. generating and applying said respective stimulation signal, having said set of selected parameters, on each of said at least one electrode, said step B further including the steps of:

configuring each of said plurality of electrodes to have a respective one of a positive polarity, a negative polarity, and an off-state polarity as selected by said patient user;

generating and applying said respective stimulation signal, having preset parameters as said set of selected parameters, on each of said at least one electrode when said patient user selects said preset parameters as said set of selected parameters; and generating and applying the respective stimulation signal having a predetermined set of parameters on each of said at least one electrode when said patient user resets said set of selected parameters;

C. inputting a corresponding rating of therapeutic effect as entered by said patient user for said set of selected parameters, said therapeutic effect resulting from application of said respective stimulation signal, having said set of selected parameters, on each of said at least one electrode;

D. inputting a corresponding normal activity as entered by said patient user, said corresponding normal activity corresponding to said set of selected parameters and said corresponding rating of therapeutic effect;

E. storing into memory said set of selected parameters, said corresponding rating of therapeutic effect, and said corresponding normal activity;

F. determining an optimum set of selected parameters that produced a highest rating of therapeutic effect across a variety of normal activities for said patient user from all ratings of therapeutic effect stored in said memory;

G. downloading said set of selected parameters, said corresponding rating of therapeutic effect, and said corresponding normal activity from said memory to a selected one of a computer and a printer; and H. displaying on a screen said set of selected parameters, said corresponding rating of therapeutic effect, and said corresponding normal activity.

* * * * *